United States Patent
DaSilva (10) Patent No.: US 7,686,267 B2
(45) Date of Patent: Mar. 30, 2010

(54) OPERATING TABLE SUPPORT CLAMP

(76) Inventor: Manuel F. DaSilva, 90 Lenihan La., East Greenwich, RI (US) 02818

( * ) Notice: Subject to any disclaimer, the term of this patent is extended or adjusted under 35 U.S.C. 154(b) by 16 days.

(21) Appl. No.: 12/037,965

(22) Filed: Feb. 27, 2008

(65) Prior Publication Data

US 2008/0203644 A1    Aug. 28, 2008

Related U.S. Application Data

(60) Provisional application No. 60/891,957, filed on Feb. 28, 2007.

(51) Int. Cl.
*A47B 96/06* (2006.01)
*E04G 3/00* (2006.01)
*F16B 1/00* (2006.01)
*G09F 7/18* (2006.01)

(52) U.S. Cl. .............. 248/229.12; 248/231.61; 248/229.14; 248/229.22; 248/228.5; 248/230.5; 248/229.24; 5/600; 5/607; 606/131

(58) Field of Classification Search ........... 248/229.12, 248/229.14, 229.22, 229.24, 228.5, 230.5, 248/231.61; 5/600, 607
See application file for complete search history.

(56) References Cited

U.S. PATENT DOCUMENTS

| | | |
|---|---|---|
| 4,355,631 A | 10/1982 | LeVahn |
| 4,742,981 A | 5/1988 | Converse |
| 4,901,964 A | 2/1990 | McConnell |
| 4,971,037 A | 11/1990 | Pelta |
| 4,993,862 A | 2/1991 | Pelta |
| 5,092,572 A * | 3/1992 | Litwak et al. .............. 5/600 |
| 5,169,106 A | 12/1992 | Rasmussen |
| 5,224,680 A | 7/1993 | Greenstein et al. |
| 5,320,314 A | 6/1994 | Bookwalter et al. |
| 5,320,444 A * | 6/1994 | Bookwalter et al. ......... 403/323 |

(Continued)

FOREIGN PATENT DOCUMENTS

DE    3436197 C1    10/1984

(Continued)

OTHER PUBLICATIONS

Medrecon, "Operating—Table Accessories to suit any table".

(Continued)

*Primary Examiner*—J. Allen Shriver, II
*Assistant Examiner*—Nkeisha J Smith
(74) *Attorney, Agent, or Firm*—Barlow, Josephs & Holmes, Ltd.

(57) ABSTRACT

A clamp assembly for use in connection with an operating table rail is disclosed. The clamp assembly includes a top clamp member, a base clamp member and an operating lever to move the top clamp member relative to the base clamp member. The base clamp member and the top clamp member include complimentary V-shaped channels that allow the clamp assembly of the present invention to be installed on the sterile side of the surgical field. The base clamp member is provided with dual guide pins and an actuator pin, extending upwards from the base clamp member and through the top clamp member. The actuator pin is affixed with a fastening means to engage the top of the actuator pin and the base clamp member together. Further, the base clamp member includes apertures for receiving various surgical support fixtures.

10 Claims, 5 Drawing Sheets

U.S. PATENT DOCUMENTS

| | | | |
|---|---|---|---|
| 5,332,184 A | | 7/1994 | Davis |
| 5,400,772 A | * | 3/1995 | LeVahn et al. ............... 600/230 |
| 5,535,973 A | | 7/1996 | Bailey et al. |
| 5,582,379 A | | 12/1996 | Keselman et al. |
| 5,597,146 A | | 1/1997 | Putman |
| 5,701,991 A | | 12/1997 | Helmetsie |
| 6,023,800 A | * | 2/2000 | Stickley ......................... 5/621 |
| 6,032,309 A | | 3/2000 | Michelson |
| 6,263,531 B1 | | 7/2001 | Navarro et al. |
| 6,370,741 B1 | | 4/2002 | Lu |
| 6,499,158 B1 | * | 12/2002 | Easterling ..................... 5/600 |
| 6,598,275 B1 | * | 7/2003 | Kolody et al. ................. 24/455 |
| 6,622,980 B2 | | 9/2003 | Boucher et al. |
| 6,629,944 B2 | | 10/2003 | Smart |
| 6,663,563 B1 | | 12/2003 | Sharratt |
| 6,704,959 B2 | | 3/2004 | Schuerch |
| 6,895,617 B2 | | 5/2005 | Zacharopoulos et al. |
| 6,896,232 B2 | * | 5/2005 | Crowell et al. ........... 248/316.4 |
| 6,912,959 B2 | * | 7/2005 | Kolody et al. ................. 108/28 |
| 7,003,827 B2 | * | 2/2006 | DeMayo ........................ 5/600 |
| 7,020,917 B1 | | 4/2006 | Kolody et al. |
| 7,156,806 B2 | | 1/2007 | Dobrovolny |
| 7,159,832 B2 | | 1/2007 | Easterling |
| 7,294,104 B2 | | 11/2007 | Person |
| 7,380,299 B1 | * | 6/2008 | DeMayo ........................ 5/648 |
| 2002/0061225 A1 | * | 5/2002 | Boucher et al. ............. 403/386 |
| 2007/0185376 A1 | | 8/2007 | Wilson et al. |

FOREIGN PATENT DOCUMENTS

| | | |
|---|---|---|
| DE | 29715607 U | 10/1997 |
| WO | 9510389 | 4/1995 |

OTHER PUBLICATIONS

Reison Medical, "Operating Table Accessories", www.reison.se/eng-accessories/10018-eng.html.

* cited by examiner

OPERATING TABLE SUPPORT CLAMP

CROSS-REFERENCE TO RELATED APPLICATIONS

This application is related to and claims priority from earlier filed U.S. Provisional Patent Application No. 60/891,957, filed Feb. 28, 2007.

BACKGROUND OF THE INVENTION

The present invention relates to a device for use in positively securing accessory devices used during surgical and other medical procedures. More specifically, the present invention relates to a clamp assembly that securely affixes to a standard surgical table to facilitate the accurate and positive positioning of accessory devices used during surgical and other medical procedures.

Orthopedic surgery on the human body generally includes procedures ranging from hand, elbow, wrist, foot and ankle surgery to fracture repair. These procedures require that the joint or limb be precisely and predictably positioned during the surgical procedure. In order to achieve the most optimum positioning, the surgeon requires a large range of positive positioning adjustments that must be easily available so that the limb or joint to be treated is initially positioned and thereafter maintained in the desired position. Not only must such a selected position be maintainable but it is also very important and often necessary that the limb be released and repositioned on demand during the course of the procedure to ensure optimum access to all areas of the joint or limb in question.

To facilitate the precise positioning required, conventional surgical tables generally include a flat patient support and a lower base for holding the patient support at a predetermined distance from the floor. The base of conventional surgical tables commonly includes a control apparatus for tilting the flat patient support through a range of orientations to facilitate performance of certain surgical procedures. Typically such flat patient supports are made of surgical stainless steel and in most cases include a set of metal side rails supported along the edges of the table for holding surgical accessories, instrumentation, and the like. Further, the side rails conform to an industry standard that dictates the cross sectional size and configuration of the rails so that surgical accessories from any vendor source can be directly connected to surgical tables built by another vendor without modification of the attachment interface.

The difficulty with most of these prior art devices is that they have numerous moving parts and components therein that make sterilization of the device virtually impossible. Since these devices cannot be sterilized, they are typically mounted directly to the metal side rails on the non-sterile side of the surgical drapes. Further, those clamps that can be sterilized and placed on the sterile side of the surgical drape generally include U-shaped or square clamping jaws that prevent them from firmly engaging the metal accessory rails when a surgical drape is positioned there between. In addition, these prior art clamps cannot engage the rail when different thicknesses or additional plies of surgical drapes are utilized. Finally, many of the prior art devices rely on a threaded rod to create the clamping tension of the device thereby transferring and bearing all of the clamping forces of the device to the small surface area of the threaded engagement. Often this ends up being the weak point in the assembly.

There is therefore a need for providing a sterile clamp to hold the various fixtures and devices, that can be installed in firm engagement with the rails on a surgical table while surgical drapes are installed there between. Further, there is a need for a sterile clamp assembly that can more firmly and reliably engage surgical table rails and reliably support a plurality of medical accessories during surgical or medical procedures.

BRIEF SUMMARY OF THE INVENTION

In this regard, the present invention provides a clamp assembly that can be engaged on the sterile side of the surgical drape that is positioned over a rail of an operating table. The clamp device of the present invention includes a top clamp member, a base clamp member and an operating lever that serves both to move apart the top clamp member relative to the base clamp member and to firmly engage the two clamp members with the support rail. The clamp device may be attached to the left or right railing by activating an excenter that brings the upper portion of the clamp to the rail until a solid, secure holding position is achieved The clamp assembly of the present invention employs a stationary base clamp member and a top moving clamp member that is activated by an adjustable excenter system to provide maximum holding on the operating table rail. The operating lever is connected with the base clamp member and permeates partially or incrementally movement of the top clamp member in the upward and downward direction. The top clamp member can be moved at a desired position providing space, between the top clamp member and the base clamp member, where the rail of an operating table can be fixed.

It is an important aspect of the present invention that the top clamp member and base clamp member are provided with V-shaped clamping channels. While V-shaped channels have been determined to be particularly effective in the context of the present invention, one skilled in the art can appreciate that other profiles exist that would also be suitable for use as clamping channels and therefore such other shapes are also believed to fall within the scope of the present invention. The V-shaped channel on the base clamp member receives one side of the rail while the corresponding V-shaped channel on the top clamp member is placed over the other side of the rail. The rail, therefore, is disposed between the V-shaped channels of the top clamp member and the base clamp member. To assure sterile conditions during the operative procedures, the clamp device is sterilized in an autoclave and is placed above the sterile cloth. The V-shaped matching grooves are adjusted by the excenter moving shaft thereby adapting to the various thickness of sterile cloth used by the surgeon.

The V-shaped channels allow the clamp assembly of the present invention to be installed onto the operating table rail on the sterile side of the surgical drape allowing the sterile surgical drape to be captured between the clamp assembly and the accessory. By positioning the clamp assembly over the surgical drape, the surgeon can easily access the clamp to make small adjustments allowing more precise positioning of the support accessories. Further the V-shaped configuration of the clamp assembly provides a greater amount of space between the operating table rail and the clamp assembly allowing more layers of surgical drapes to be accommodated therein. The clamp of the present invention has been tested with up to 10 plies of surgical drape with no creep or loosening of the clamp.

The base clamp member is provided with an operating lever, dual guide pins and an actuator pin extending upwards from the upper surface of the base clamp member. Further, the top clamp member is provided with corresponding openings for receiving the guide pins and an opening for receiving the actuator pin. The dual guide pins serve to reliably position the top clamp member and the base clamp member in a parallel fashion while operating while preventing their shifting and/or torquing relative to one another once the clamp assembly is positioned and fastened. The actuator pin having a lower end engaged with the operating lever and an upper end having a threaded fastener. The activating shaft is operating the actuator pin via the excenter to move the upper clamp down to the holding position. Further, a mean for adjusting the length of the actuator pin thereby controlling the overall fastening tension is provided on the top clamp member to tighten or loosen the engagement between top and base clamp members. The operating lever moves 90 degrees to the right or to the left (clockwise or counterclockwise), from a low (engaged) to a high position (disengaged). The up and down position is created by turning the activating shaft which in turn rotates the excenter inside the actuator pin. The upper clamp base will move down or up until a secure holding position is achieved.

The operating lever partially extends into the base clamp member and is operatively engaged with the actuator pin. The operating lever consists of an activating shaft including an eccentrically positioned locking pin or excenter engaged with the lower end of the actuator pin. Rotation of the operating lever and in turn the activating shaft in clockwise direction causes the locking pin to be displaced upwardly within the groove in the actuator pin. This moves the actuator pin upwardly causing the top clamp member to also be displaced upwardly. Further, rotation of the operating lever and in turn the activating shaft in the counter-clockwise direction, causes the locking pin to be displaced downwardly within the groove in the actuator pin. This draws the actuator pin downwardly causing the top clamp member to be drawn downwardly.

It is another important aspect of the invention that the base clamp member is provided with apertures to receive and retain surgical support fixtures. These apertures may be provided on any face of the lower jaw including the side surfaces allowing greater versatility and adjustability of the positioning accessories. Further, such apertures may also be provided on the top clamping member and still fall within the scope and spirit of the present invention.

Further, a safety mechanism has been provided to prevent the accidental rotation or loosening of the operating lever once the clamp assembly is installed. The safety key is provided on the base clamp member. Once the clamp assembly is installed, the safety pin is rotated to prevent further movement of the activating shaft. Rotation of the safety pin in clockwise or anticlockwise direction cause the safety pin to move at the desired downward or upward position to fix the position activating shaft. Once the safety pin is in contact with the activating shaft, it blocks further rotation of the activating shaft.

Accordingly, it is an object of the present invention to provide a clamp assembly for an operating table to be used in a sterile environment to hold different fixtures and devices. It is a further object of the present invention to provide a clamp assembly that firmly and reliably engages the left and right rails of an operating table to reliably and securely hold different fixtures and devices in the desired position.

These together with other objects of the invention, along with various features of novelty that characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In the drawings which illustrate the best mode presently contemplated for carrying out the present invention.

DETAILED DESCRIPTION OF THE INVENTION

Now referring to the drawings, an operating room table clamp is depicted that securely attaches to the right or left operating table rail. Once in place, various fixtures or devices may be attached onto this clamp to stabilize an upper limb, lower limb, surgical retractors and various other holding devices used during operative procedures. The clamp assembly according to one embodiment of the present invention includes a top clamp member, a base clamp member and an operating lever. The top clamp member can be moved at a desired position providing a space between the top clamp member and the base clamp member, where the rail of an operating table can be fixed. In addition, the clamp assembly can also serve as an attachment interface for apparatus other than limb positioning, such as for example, a table that can directly attach to the surgical table.

Figure 1:
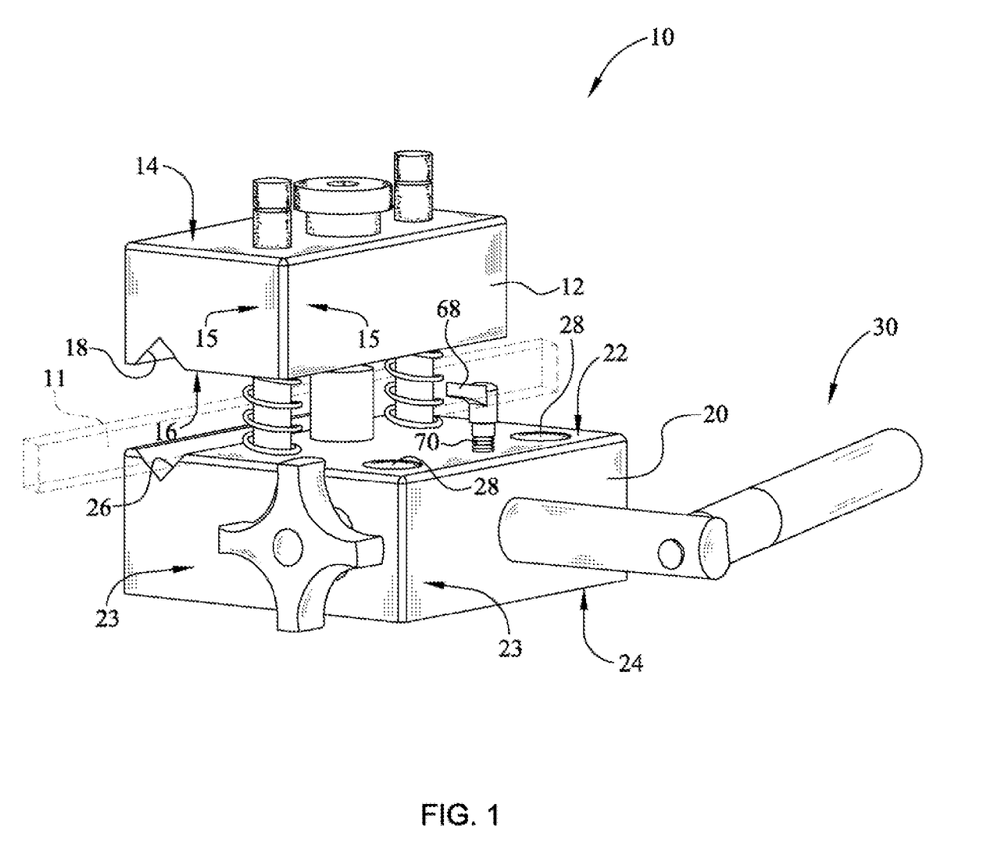
FIG. 1 illustrates a perspective view of a clamp assembly of the present invention.

Referring to FIG. 1, a perspective view of a clamp assembly according to an exemplary embodiment of the present invention is represented. The clamp assembly (10) of the present invention can be affixed to the rail of an operating table. The clamp assembly (10) includes a top clamp member (12), a base clamp member (20) and an operating lever (30). The operating lever (30) is connected with the base clamp member (20) and actuates movement of the top clamp member (12) in the upward and downward direction. The top clamp member (12) can be moved to a desired position providing a space, between the top clamp member (12) and the base clamp member (20), where the rail (11) of an operating table is fixed. In an assembled configuration, the base clamp member (20) is placed on one side of the rail (11) and the top clamp member (12) is placed on the opposite side of the rail (11), hence the rail (11) is disposed between the top clamp member (12) and the base clamp member (20).

In an embodiment shown above, the rail conforms to a rectangular shape edges. However the clamp assembly of the present invention can be affixed with a rail of different cross sectional size and configuration available as per industry standards.

Still referring to FIG. 1, the base clamp member (20) includes an upper surface (22), side surfaces (23) and a lower surface (24). The upper surface (22) of the base clamp member (20) is configured to include a first V-shaped channel (26).

The V-shaped channel (26) on the upper surface (22) of the base clamp member (20) allows the clamp assembly (10) to engage with one side, preferably bottom side, of the operating table rail (11). Further, the base clamp member (20) is provided with apertures (28) to receive and retain surgical support equipments. These apertures may be provided on any surface of the base clamp member including the upper surface (22), the side surfaces (23) or the lower surface (24) allowing greater versatility and adjustability to the of the positioning accessories.

Similarly, the top clamp member (12) includes an upper surface (14), side surfaces (15) and a lower surface (16). The lower surface (16) of the top clamp member (12) having a second V-shaped channel (18). The V-shaped channel (18) on the top clamp member (12) is complementary with the V-shape channel (26) on the upper surface of the base clamp member (20). While V-shaped channels (18, 26) have been determined to be particularly effective in the context of the present invention, one skilled in the art can appreciate that other profiles exist, such as U-shaped or square, that would also be suitable for use as clamping channels and therefore such other shapes are also believed to fall within the scope of the present invention.

Figure 2:
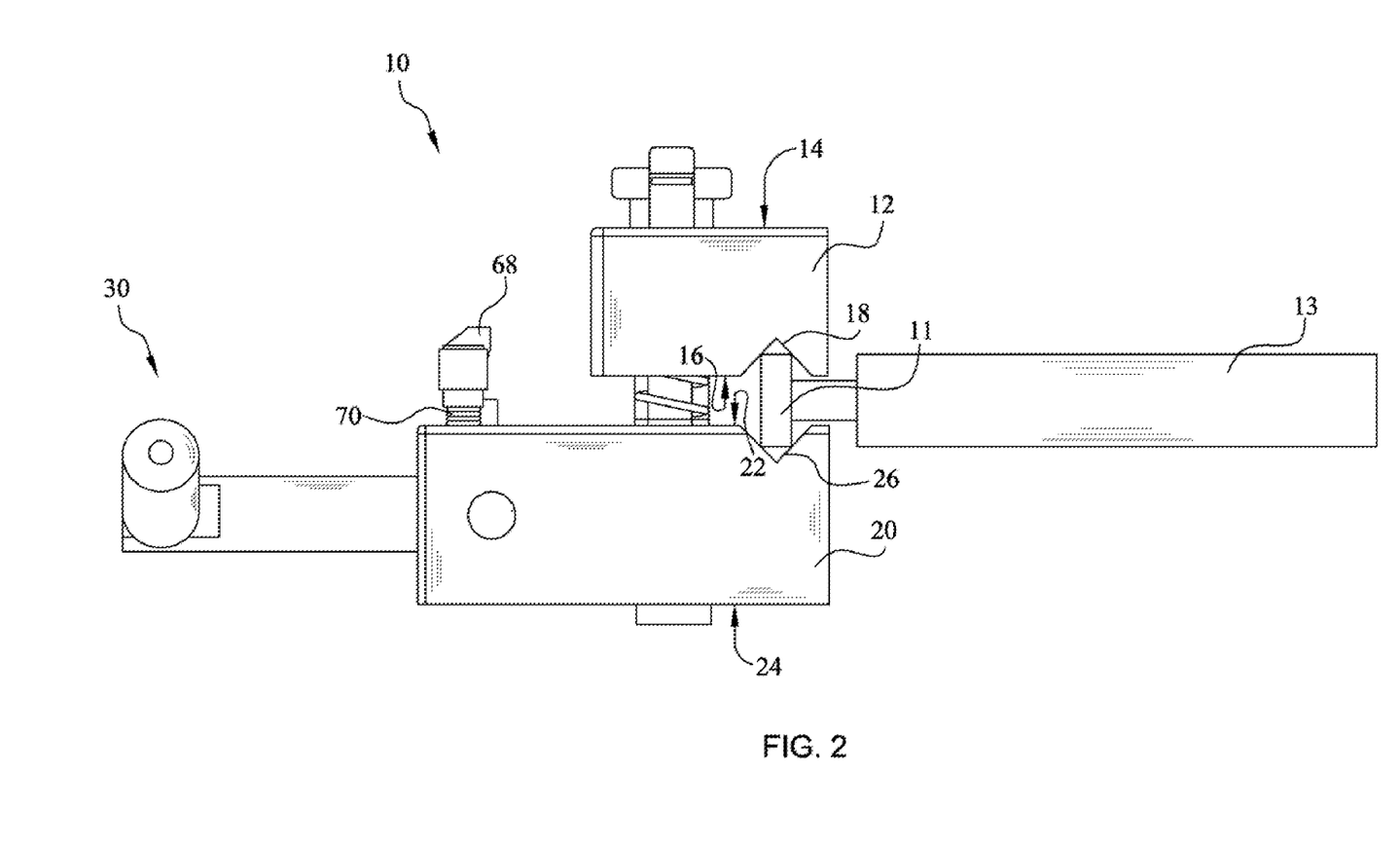
FIG. 2 illustrates a side view of the clamp assembly of the present invention in an installed position.

Turning now to FIG. 2, a side view of a clamp assembly according to an embodiment of the present invention is shown affixed to a rail of an operating table. In an assembled position, the rail (11) of the operating table (13) is placed between the top clamp member (12) and the base clamp member (20). The V-shaped channel (26) on the upper surface of the base clamp member (20) receives one side of the rail (11). The corresponding V-shaped channel (18) on the lower surface of the top clamp member (12) is placed over the other side of the rail (11). The rail (11), therefore, is disposed between the V-shaped channels of the top clamp member (12) and the base clamp member (20).

It is an important aspect of the present invention that the top and base clamp members are provided with complimentary V-shaped channels. The V-shaped channels allow the clamp assembly of the present invention to be installed onto the accessory rail on the sterile side of the surgical drape allowing the sterile surgical drape to be captured between the clamp assembly and the accessory rail thereby leaving the clamp assembly above the drape. By positioning the clamp assembly over the surgical drape, the surgeon can easily access the clamp to make small adjustments, allowing more precise positioning of the surgical support equipments. Further, the V-shaped configuration of the clamp assembly provides a greater amount of space between the accessory rail and the clamp assembly allowing more amount of surgical drapes to accommodate therein. The clamp of the present invention has been tested with up to 10 plies of surgical drape with no creep or loosening of the clamp. Also, the V-shaped configuration of the clamp assembly reduces tension on the surgical drape preventing it from tearing during the surgical or medical procedures or when clamp assembly is tightened or loosened or move to a different place on the rail.

Figure 3:
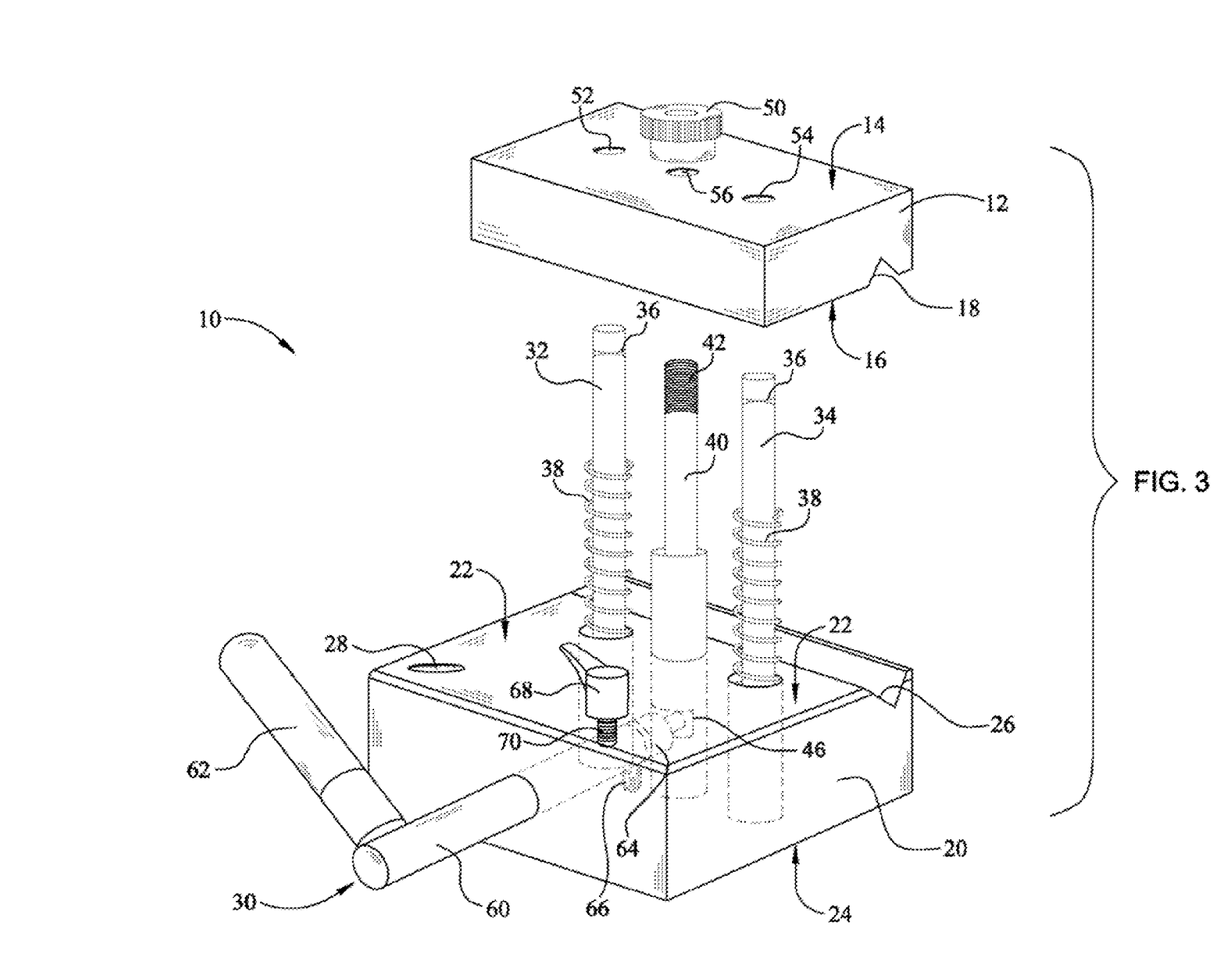
FIG. 3 shows an exploded view of the clamp assembly of the present invention.

FIG. 3 shows an exploded view of the clamp assembly (10) of FIG. 1. The base clamp member (20) is provided with an operating lever (30), dual guide pins (32, 34) and an actuator pin (40) extending upwards from the upper surface (22) of the base clamp member (20). Further, the top clamp member is provided with corresponding openings (52, 54) for receiving the guide pins and an opening (56) for the actuator pin.

The dual guide pins (32, 34) extends upward from the upper surface of the base clamp member (20) pierced through the openings (52, 54) on the top clamp member (12) and finally received on the upper surface (14) of the top clamp member (12). The portion of the guide pins (32, 34) received on the upper surface of the top clamp member (12) is provided with a locking washer (36) which prevents the movement of the guide pins once the clamp assembly is assembled with the rail. The guide pins (32, 34) serve to reliably position the top clamp member (12) and the base clamp member (20) and prevent their shifting and/or torquing relative to one another once the clamp assembly is assembled. In an embodiment shown, the guide pins (32, 34) are provided with concentric springs (38) that serve to spring bias the top clamp member (12) and base clamp member (20) apart from one another.

The actuator pin (40) also extends upwardly from the upper surface (22) of the base clamp member (20), having a lower end and an upper end. The lower end of the actuator pin extends into the interior of the base clamp member and is operatively engaged with the operating lever or excenter. The upper end of the actuator pin extends through the opening (56) of the top clamp member (12) and includes a threaded end (42) for receiving a threaded fastener adjacent the upper surface (14) of the top clamp member (12). The actuator pin on the upper surface of the top clamp member is engaged with a means for adjustably fastening (50) onto the top threaded end of the actuator pin. The relative distance between the top and base clamp member is incrementally adjusted by tightening or loosening the means for fastening (50) and therefore controlling overall clamping tension applied between the top and base clamp members.

In an embodiment shown above, the mean of fastening (50), a knurled nut is used to fasten together the top and base clamp member. However, various others means for fastening known to a person of ordinary skill in the art can be used to fasten the top and base clamp members.

As shown in FIG. 3, the operating lever (30) extends into the base clamp member (20) and is operatively engaged with the lower end of the actuator pin (40). The operating lever (30) consists of an activating shaft (60) and a handle (62). The activating shaft (60) has an eccentrically mounted locking pin (64) extending from a distal end thereof that engages with the lower end of the actuator pin (40). Further, a set screw (66) is provided that engages a ridge on the activating shaft (60) and facilitates rotation of the activating shaft (60) and the locking pin (64) preventing disengagement between the eccentrically mounted locking pin (64) from the actuator pin (40). Operation on the operating lever (30) and in turn activating shaft (60) cause the locking pin (64) to displace the actuator pin (40) at the desired position, which in turn moves the top clamp member.

Figure 4:
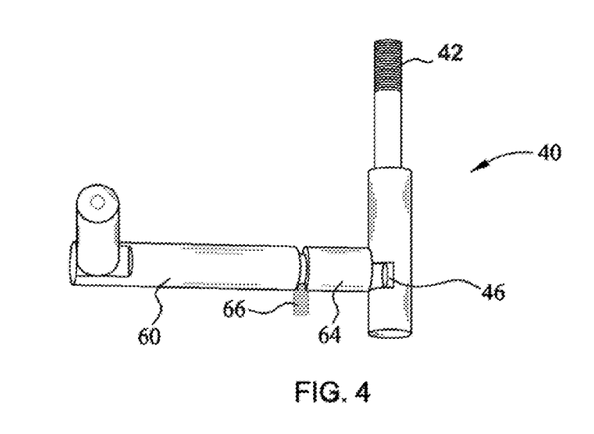
FIG. 4 is a plan view showing engagement between an operating lever and an actuator pin of the clamp assembly of the present invention.

FIG. 4 shows an engagement between an activating shaft (60) and an actuator pin (40). The activating shaft (60) includes an eccentrically mounted locking pin (64) and a setscrew (66) facilitating rotation of the locking pin (64) and thereby the activating shaft (60). The lower end of the actuator pin (40) has a slotted opening (46) to engage with the eccentrically mounted locking pin (64). The slotted opening is further provided with a groove (48) to fix the locking pin (64). Rotation of the activating shaft (60) in clockwise or counter-clockwise direction causes movement of the actuator pin (40) enabling it to move partially or incrementally in upward or downward direction.

Figures 5A, 5B:
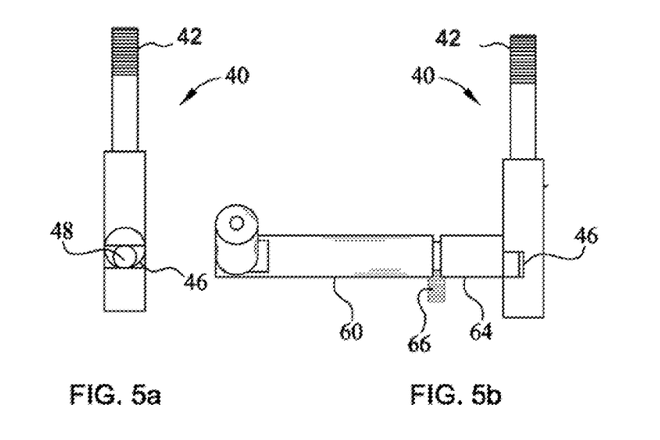
FIGS. 5a and 5b is a plan view illustrating a mechanism for moving the actuator pin in upward direction.
Figure 6A:
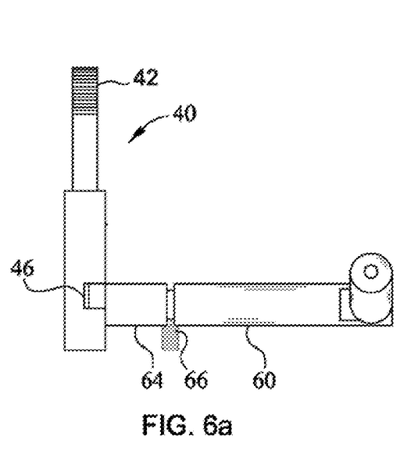
FIGS. 6a and 6b is plan view illustrating a mechanism for moving the actuator pin in downward direction.
Figure 6B:
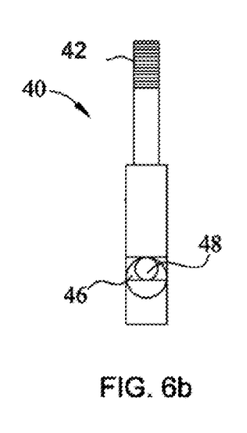

FIGS. 5a and 5b illustrates mechanism to move the actuator pin of FIG. 4 in upward direction. The rotation of the activating shaft (60) in clockwise direction causes the locking pin (64) to be displaced upwardly within the groove (48) of the actuator pin (40). This causes the actuator pin (40) to move in upward direction. Further, rotation of the activating shaft (60) in the anti-clockwise direction, as shown in FIGS. 6a and 6b, causes the locking pin (64) to be displaced downwardly within the groove (48) of the actuator pin (40). This draws the actuator pin (40) in downward direction.

In an embodiment described above, the operable engagement between the operating lever and the actuator pin is a camming action. However, the present invention is not restricted to the above described engagement. Various other means of engagement known to a person of ordinary skill in the art can be used to engage the operating lever and the actuator pin.

It is another important aspect of the present invention that the clamp assembly is provided with a safety mechanism. The safety mechanism prevents the accidental rotation or loosening of the operating lever and hence provides stability to the clamp assembly once it is installed.

Figure 7:
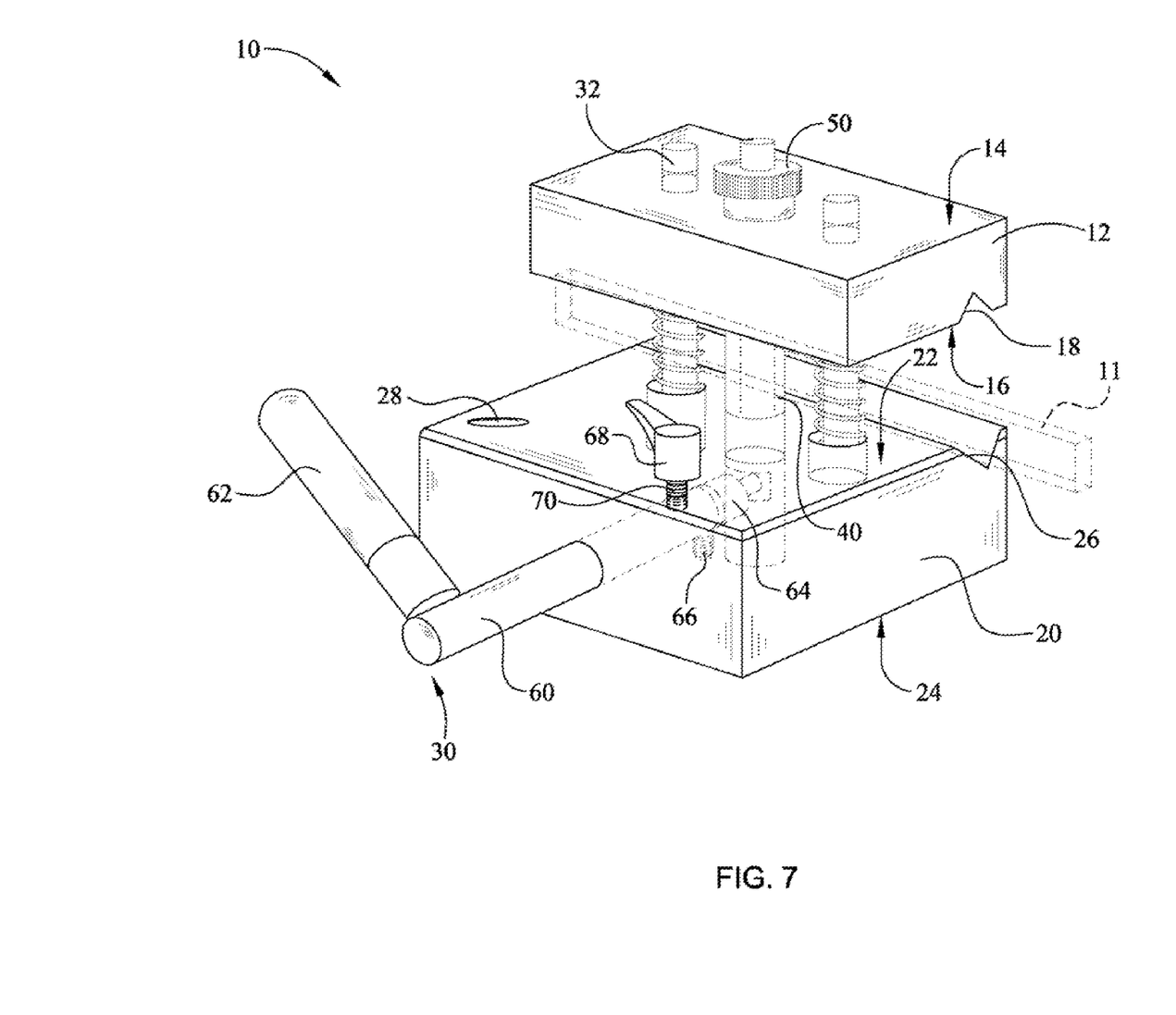
FIG. 7 represents a clamp assembly of the present invention in an installed position.

Referring to FIG. 7, a clamp assembly of the present invention in an installed position is shown. In order to assemble the clamp assembly of the present invention, the operating lever is rotated to move the top clamp member in the upward direction up to a desired position such that the rail can be placed within the gap generated between the top and bottom clamp member. The V-shaped channel of the top and bottom clamp members are then received about the rail. The top clamp member can be moved downward using the operating lever to place the V-shaped channel of the top clamp member into operative engagement with on other side of the rail. The top and base clamp members are then fastened using the mean for fastening. Finally a safety pin is engaged with the activating shaft of the operating lever to prevent further rotation of the activating shaft and hence providing stability to the clamp assembly.

Referring to FIG. 7, the clamp assembly (10) of the present invention in an installed position is represented. The operating table rail (11) is disposed between the V-shaped channel of the top clamp member (12) and the base clamp member (20). The means of fastening (50) fastens the top clamp member (12) with the bottom clamp member (20) providing a tension between the clamp members. Further, a safety key (68) is provided on the upper surface of the base clamp member (20). The safety key (68) can be provided on the bottom surface of the base clamp member (20). Once the clamp assembly is installed, the safety key (68) is rotated to prevent further movement of the activating shaft (60). Rotation of the safety key (68) in clockwise or counterclockwise direction causes a safety pin (70) to move at the desired downward or upward position so as to affix with the activating shaft (60). Once the safety-pin (70) is affixed with the activating shaft (60), it blocks further rotation of the activating shaft (60).

In an embodiment shown above, the safety pin is a threaded key. Various other safety mechanisms to prevent the movement of the activating shaft, known to a person of ordinarily skill in the art, can be applied and are well within the scope of the present invention.

Various other embodiments are possible within the spirit of the invention and the aforementioned examples and embodiments are just meant to be for explanatory purposes, and in no way intend to bind the invention in any manner. The clamp assembly of the present invention can be made from various kinds of materials available in the field and known to a person skilled in the art. Preferably the clamp assembly of the present invention is made of material that can withstand the temperature and pressure conditions for autoclaving. The invention intends to cover all the equivalent embodiments and is limited only by the appended claims.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A clamp assembly for supporting accessories from an operating table accessory rail comprising:
    a base clamp member having an upper surface and a lower surface, the upper surface having an engagement channel to engage on one side of an operating table rail;
    a top clamp member having an upper surface and a lower surface, the lower surface having a second engagement to engage on other side of the operating table rail;
    at least one actuator pin having a lower end, a groove formed in the at least one actuator pin adjacent the lower end thereof and a threaded upper end, the threaded upper end extending through the top clamp member and the lower end of said at least one actuator pin extending into the interior of the base clamp member;
    and operatively engaged with an activating shaft
    an operating lever having a handle connected to the activating shaft with a distal end and a locking pin extending from and positioned eccentrically relative to the distal end, the distal end extending within the base clamp member such that the locking pin is operatively engaged with the groove in said at least one actuator pin such that rotation of the activating shaft causes movement of the top clamp member relative to the bottom clamp member; and
    a retention means received on the threaded end of said at least one actuator pin, the retention means adjustable in a manner that controls the clamping force between the top clamp member and the base clamp member.

2. The clamp assembly as claimed in claim 1, further comprising:
    a locking mechanism to prevent accidental rotation of the activating shaft.

3. The clamp assembly as claimed in claim 2, wherein the locking mechanism includes a screw extending downwardly from the upper surface of the base clamp member to fasten the activating shaft.

4. The clamp assembly as claimed in claim 1, further comprising:
    a set screw engaging the activating shaft and said at least one actuator pin.

5. The clamp assembly as claimed in claim 1 wherein the engagement channels have a shape selected from the group consisting of: V-shaped grooves, U-shaped grooves and square grooves.

6. The clamp assembly as claimed in claim 1, further comprising:
    dual spring loaded guide pins extending upwardly from the upper surface of the base clamp member and into the top clamp member.

7. The clamp assembly as claimed in claim 1, wherein the retention means is a knurled nut engaged with the threaded upper end of said at least one actuator pin.

8. The clamp assembly as claimed in claim 1, wherein the base clamp member includes apertures therein to receive and retain surgical support equipment.

9. The clamp assembly as claimed in claim 1, wherein the top clamp member includes apertures therein to receive and retain surgical support equipment.

10. The clamp assembly as claimed in claim 1, wherein the clamp assembly is made of a material that withstands surgical autoclave temperatures.

* * * * *